US011547405B2

(12) United States Patent
Scampoli et al.

(10) Patent No.: US 11,547,405 B2
(45) Date of Patent: Jan. 10, 2023

(54) SURGICAL STAPLING DEVICE

(71) Applicant: Covidien LP, Mansfield, MA (US)

(72) Inventors: David Scampoli, South Glastonbury, CT (US); Jon A. Wink, Haddam, CT (US)

(73) Assignee: Covidien LP, Mansfield, MA (US)

( * ) Notice: Subject to any disclaimer, the term of this patent is extended or adjusted under 35 U.S.C. 154(b) by 3 days.

(21) Appl. No.: 17/313,181

(22) Filed: May 6, 2021

(65) Prior Publication Data

US 2021/0361283 A1 Nov. 25, 2021

Related U.S. Application Data

(60) Provisional application No. 63/028,908, filed on May 22, 2020.

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01); *A61B 34/30* (2016.02); *A61B 90/98* (2016.02); *G01R 31/36* (2013.01); *A61B 17/00234* (2013.01); *A61B 17/115* (2013.01);
(Continued)

(58) Field of Classification Search
CPC ................ A61B 17/068; A61B 17/072; A61B 17/07207; A61B 17/115; A61B 17/00234; A61B 17/32002; A61B 2017/07214; A61B 34/30; A61B 34/71; A61B 34/74; A61B 34/76; A61B 90/90; A61B 90/98; H01M 50/572; H01M 50/20; H01M 50/213; H01M 10/48; H01R 12/716; H01R 13/52; H01R 13/5224; H05K 5/0056; H05K 5/0069;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

European Search Report dated Oct. 14, 2021, issued in corresponding EP Appln. No. 21174898, 7 pages.

*Primary Examiner* — Scott A Smith
(74) *Attorney, Agent, or Firm* — Carter, DeLuca & Farrell LLP

(57) ABSTRACT

A surgical stapling device includes a handle assembly, an adapter assembly, and a reload assembly that is releasably secured to the adapter assembly to facilitate replacement of the reload assembly after each use of the stapling device. The reload assembly includes an authentication chip and printed circuit board assembly that is constructed to provide electrical contacts that are self-supporting to allow for automated assembly of the electrical contacts and provide a more reliable, robust electrical connection between the electrical contacts and the chip.

20 Claims, 9 Drawing Sheets

(51) Int. Cl.
  A61B 90/98 (2016.01)
  G01R 31/36 (2020.01)
  A61B 34/30 (2016.01)
  H01M 50/572 (2021.01)
  H05K 5/02 (2006.01)
  H01M 10/48 (2006.01)
  A61B 17/00 (2006.01)
  H01M 50/20 (2021.01)
  G16H 20/40 (2018.01)
  A61B 17/115 (2006.01)
  H05K 5/00 (2006.01)
  A61B 17/32 (2006.01)
  H01R 13/52 (2006.01)
  A61B 34/00 (2016.01)

(52) U.S. Cl.
  CPC ......... A61B 17/32002 (2013.01); A61B 34/74 (2016.02); A61B 2017/07214 (2013.01); G01R 31/3648 (2013.01); G16H 20/40 (2018.01); H01M 10/48 (2013.01); H01M 50/20 (2021.01); H01M 50/572 (2021.01); H01R 13/52 (2013.01); H05K 5/006 (2013.01); H05K 5/0221 (2013.01)

(58) Field of Classification Search
  CPC .... H05K 5/0221; H05K 5/0275; G01R 31/36; G01R 31/3648
  USPC ..... 227/19, 175.1, 176.1, 180.1; 606/1, 139, 606/219
  See application file for complete search history.

(56) References Cited

U.S. PATENT DOCUMENTS

| | | | |
|---|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Faheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |

(56) References Cited

U.S. PATENT DOCUMENTS

| | | |
|---|---|---|
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |

(56) References Cited

U.S. PATENT DOCUMENTS

| | | | |
|---|---|---|---|
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |
| 7,770,776 | B2 | 8/2010 | Chen et al. |
| 7,771,440 | B2 | 8/2010 | Ortiz et al. |
| 7,776,060 | B2 | 8/2010 | Mooradian et al. |
| 7,793,813 | B2 | 9/2010 | Bettuchi |
| 7,802,712 | B2 | 9/2010 | Milliman et al. |
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,479,968 | B2 | 7/2013 | Hodgkinson et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,627,995 | B2 | 1/2014 | Smith et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,646,674 | B2 | 2/2014 | Schulte et al. |
| 8,662,370 | B2 | 3/2014 | Takei |
| 8,663,258 | B2 | 3/2014 | Bettuchi et al. |
| 8,672,207 | B2 | 3/2014 | Shelton, IV et al. |
| 8,672,931 | B2 | 3/2014 | Goldboss et al. |
| 8,672,951 | B2 | 3/2014 | Smith et al. |
| 8,678,264 | B2 | 3/2014 | Racenet et al. |
| 8,679,137 | B2 | 3/2014 | Bauman et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,695,864 | B1 | 4/2014 | Hausen |
| 8,708,212 | B2 | 4/2014 | Williams |
| 8,733,611 | B2 | 5/2014 | Milliman |
| 8,733,615 | B2 | 5/2014 | Nalagatla et al. |
| 8,746,531 | B2 | 6/2014 | Wenchell et al. |
| 8,746,532 | B2 | 6/2014 | Nalagatla et al. |
| 8,783,543 | B2 | 7/2014 | Shelton, IV et al. |

(56) References Cited

U.S. PATENT DOCUMENTS

| | | |
|---|---|---|
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0018978 A1 | 1/2005 | Nevo et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |

(56) References Cited

U.S. PATENT DOCUMENTS

| | | |
|---|---|---|
| 2010/0051668 A1 | 3/2010 | Milliman et al. |
| 2010/0084453 A1 | 4/2010 | Hu |
| 2010/0163598 A1 | 7/2010 | Belzer |
| 2010/0200636 A1* | 8/2010 | Zemlok ............... A61B 17/10 227/175.1 |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0246477 A1* | 9/2014 | Koch, Jr. ............ A61B 34/30 227/180.1 |
| 2014/0284370 A1 | 9/2014 | Sahin |
| 2014/0305991 A1* | 10/2014 | Parihar ............. A61B 17/115 227/176.1 |
| 2015/0053744 A1* | 2/2015 | Swayze ............... G16H 20/40 227/176.1 |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2015/0342601 A1* | 12/2015 | Williams .......... A61B 17/068 227/175.1 |
| 2016/0132026 A1* | 5/2016 | Wingardner .......... G05B 15/02 700/275 |
| 2016/0249915 A1* | 9/2016 | Beckman ........... H01M 50/572 227/175.1 |
| 2018/0353186 A1* | 12/2018 | Mozdzierz ........... A61B 17/072 |
| 2022/0133303 A1* | 5/2022 | Huang ............ A61B 17/07207 227/175.1 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| DE | 19755767 A1 | 6/1999 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2008107918 A1 | 9/2008 |

* cited by examiner

SURGICAL STAPLING DEVICE

CROSS-REFERENCE TO RELATED APPLICATIONS

This application claims the benefit of and priority to U.S. Provisional Patent Application No. 63/028,908, filed May 22, 2020, the entire contents of which is incorporated by reference herein.

FIELD

This technology is generally related to surgical stapling devices and, more particularly, to surgical stapling devices with reusable adapter assemblies and disposable reload assemblies.

BACKGROUND

Surgical stapling devices for suturing tissue are well known in the art and typically include a handle assembly, an adapter assembly, and an end effector supported on the adapter assembly for treating tissue. Such stapling devices are capable of suturing tissue more quickly than traditional suturing techniques to reduce time required to perform surgical procedures and reduce trauma to a patient.

In order to reduce costs associated with surgical procedures that require tissue to be sutured, the end effector of the surgical stapling device may form part of a reload assembly that is releasably coupled to the adapter assembly and disposable to facilitate reuse of the handle assembly and the adapter assembly. In some cases, the adapter and handle assemblies can be configured to be used with different types or sizes of reload assemblies. The reload assembly may include an authentication chip that communicates with the adapter assembly and the handle assembly when the reload is coupled to the adapter assembly to, inter alia, ensure that the reload assembly is compatible with the adapter and handle assemblies and to allow the handle assembly to properly actuate the particular reload assembly.

In such devices, the adapter and the reload assemblies include electrical contacts that mate when the reload assembly is coupled to the adapter assembly to electrically couple the authentication chip to the adapter assembly. If the electrical connection between the adapter assembly and reload assembly is compromised, the surgical device will not operate.

SUMMARY

In aspects, this disclosure generally relates to a surgical stapling device including a handle assembly, an adapter assembly, and a reload assembly that is releasably secured to the adapter assembly to facilitate replacement of the reload assembly after each use of the stapling device. The reload assembly includes an authentication chip and printed circuit board assembly that includes electrical contacts that are coupled to the adapter assembly and communicate with the handle assembly when the reload is coupled to the adapter assembly. The construction of the authentication chip and printed circuit board (PCB) assembly described herein provides electrical contacts that are self-supporting to allow for automated assembly of the electrical contacts and provides a more reliable, robust electrical connection between the electrical contacts and the chip.

One aspect of the disclosure is directed to a chip and printed circuit board assembly that includes a housing, a printed circuit board, an authentication chip, electrical contacts, and a cap. The housing includes a body that defines a cavity and has open proximal and distal ends that communicate with the cavity. The body includes a transverse wall that extends across the cavity and has a proximal side and a distal side. The transverse wall defines spaced openings that extend through the transverse wall and are configured to receive conductive prongs of a plug. The printed circuit board is supported within the cavity of the housing on the distal side of the transverse wall. The authentication chip is supported on and is electrically coupled to the printed circuit board. The electrical contacts are also supported on and are electrically coupled to the printed circuit board. Each of the electrical contacts defines a slot. The slots are aligned with the openings in the transverse wall and are dimensioned to receive the conductive prongs of the plug. The cap is received within the distal end of the body and engages the printed circuit board to retain the printed circuit board, the authentication chip, and the electrical contacts within the cavity.

Another aspect of the disclosure is directed to a reload assembly that includes a shell housing, a staple cartridge, a pusher assembly, and a chip and printed circuit board assembly. The shell housing includes an outer annular body portion and an inner annular body portion that define an annular cavity. The staple cartridge is supported on the shell housing and supports a plurality of staples. The pusher assembly is supported within the annular cavity and is movable from a retracted position to an advanced position to eject staples from the staple cartridge. The chip and printed circuit board assembly is supported on the shell housing and includes a housing, a printed circuit board, an authentication chip, electrical contacts, and a cap. The housing includes a body that defines a cavity and has open proximal and distal ends that communicate with the cavity. The body includes a transverse wall that extends across the cavity and has a proximal side and a distal side. The transverse wall defines spaced openings that extend through the transverse wall and are configured to receive conductive prongs of a plug. The printed circuit board is supported within the cavity of the housing on the distal side of the transverse wall. The authentication chip is supported on and is electrically coupled to the printed circuit board. The electrical contacts are also supported on and are electrically coupled to the printed circuit board. Each of the electrical contacts defines a slot. The slots are aligned with the openings in the transverse wall and are dimensioned to receive the conductive prongs of the plug. The cap is received within the distal end of the body and engages the printed circuit board to retain the printed circuit board, the authentication chip, and the electrical contacts within the cavity.

In aspects of the disclosure, the body is defined by walls having inner surfaces that include alignment ribs that engage and properly position the printed circuit board within the housing.

In some aspects of the disclosure, the body includes walls that define wall openings and the cap includes tabs that are received within the wall openings in a snap-fit manner to secure the cap to the housing.

In certain aspects of the disclosure, each of the electrical contacts has a tuning fork shape and includes first and second elongate contact portions that are spaced from each other to define the slot of the respective electrical contact.

In aspects of the disclosure, the first and second elongate contact portions of each of the electrical contacts are configured to define the slot to have a converging-diverging configuration.

In some aspects of the disclosure, the first and second elongate contact portions of each of the electrical contacts are connected by a base having a prong.

In certain aspects of the disclosure, the printed circuit board defines bores that receive the prongs of the electrical contacts.

In aspects of the disclosure, the printed circuit includes a surface having support pads, and the authentication chip is soldered to the support pads.

In some aspects of the disclosure, the transverse wall includes tapered walls that define the openings in the transverse wall and taper inwardly towards the openings in the transverse wall in a distal direction.

In certain aspects of the disclosure, the housing includes a securement ring that is configured to secure the chip and printed circuit board assembly to a surgical device.

In aspects of the disclosure, the housing of the chip and printed circuit board assembly includes a securement ring that is configured to secure the housing of the chip and printed circuit board assembly to the inner annular body portion of the shell housing.

Other features of the disclosure will be appreciated from the following description.

BRIEF DESCRIPTION OF DRAWINGS

Various aspects of the disclosure are described herein below with reference to the drawings, wherein.

DETAILED DESCRIPTION

Figure 1:
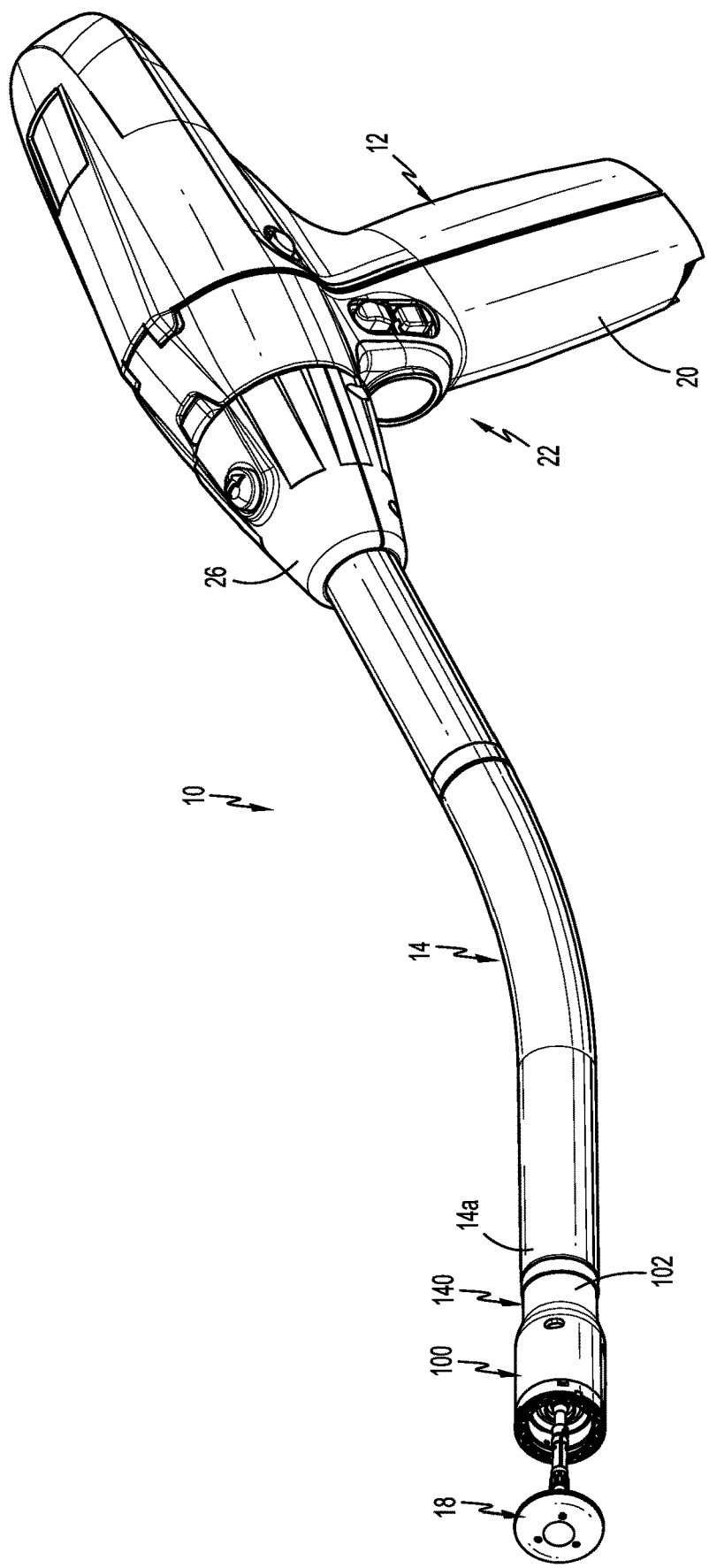
FIG. 1 is a side perspective view of a surgical stapling device including aspects of the disclosure.

The disclosed stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through a small diameter incision or cannula. Further, the term "clinician" is used generally to refer to medical personnel including doctors, nurses, and support personnel.

FIG. 1 illustrates a surgical stapling device 10 including aspects of the disclosure shown generally as stapling device 10. The stapling device 10 includes a handle assembly 12, an adapter assembly 14, an anvil assembly 18, and a reload assembly 100. The handle assembly 12 includes a stationary grip 20 that supports actuation buttons 22 for controlling operation of various functions of the stapling device 10 including approximation of the reload and anvil assemblies 100 and 18, respectively, firing of staples from the reload assembly 100, and cutting or coring of tissue. The adapter assembly 14 includes an anvil retainer 24 (FIG. 3) and is coupled to the handle assembly 12 by a rotation knob 26. The rotation knob 26 is rotatably supported on the handle assembly 12 to facilitate rotation of the adapter assembly 14 and the reload assembly 100 in relation to the handle assembly 12. The anvil assembly 18 is supported on the anvil retainer 24 (FIG. 3) of the adapter assembly 14 and is movable in relation to the reload assembly 100 between open and clamped positions. The reload assembly 100 includes a proximal portion 102 (FIG. 1) that is releasably coupled to a distal portion 14a of the adapter 14 to facilitate removal and replacement of a spent or fired reload assembly and reuse of the handle assembly 12 and adapter assembly 14.

The stapling device 10 is illustrated as an electrically powered stapling device and includes an electrically powered handle assembly 12. In aspects of the disclosure, the stationary handle 20 of the handle assembly 12 supports a battery pack or one or more batteries (not shown) that provide power to the stapling device 10. The adapter assembly 14 translates power from the handle assembly 12 to the reload assembly 100 and to the anvil assembly 18 to actuate the reload assembly 100. Examples of electrically powered stapling devices can be found in U.S. Pat. No. 9,055,943 (the '943 Patent), U.S. Pat. No. 9,023,014 (the '014 Patent), and U.S. Publication Nos. 2018/0125495, and 2017/0340351.

Alternately, it is envisioned that aspects of the disclosure could also be incorporated into a manually powered stapling device such as disclosed in U.S. Pat. No. 7,303,106 (the '106 Patent) or a stapling device that is configured for use with a robotic system such as disclosed in U.S. Pat. No. 9,962,159 (the '159 Patent) that does not include a handle assembly.

Figure 2:
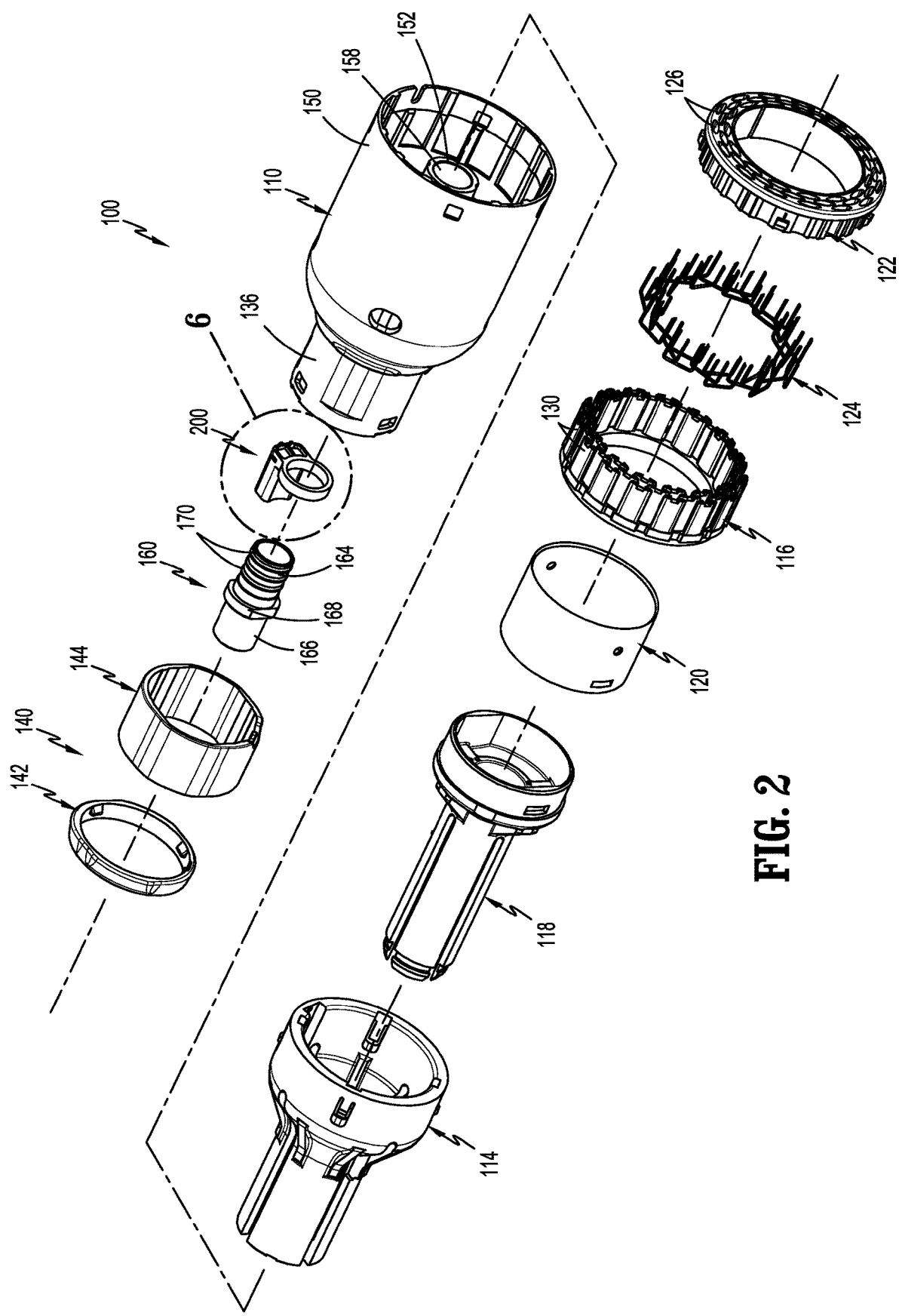
FIG. 2 is a side perspective exploded view of the reload assembly of the surgical stapling device shown in FIG. 1.

FIG. 2 illustrates the reload assembly 100 which includes a shell housing 110, a pusher assembly including an annular pusher 114 and a staple pushing member 116, a knife carrier 118, an annular knife 120 supported on the knife carrier 118, a staple cartridge 122, and a plurality of staples 124 supported within the staple cartridge 122. The staple cartridge 122 is annular and defines annular rows of staple pockets 126. Each of the staple pockets 126 supports one of the plurality of staples 124. The annular pusher 114 has a distal portion that abuts a proximal portion of the staple pushing member 116 such that distal movement of the pusher 114 within the shell housing 110 from a retracted position to an advanced position causes distal movement of the staple pushing member 116. The staple pushing member 116 of the reload 100 has a plurality of fingers 130. Each of the plurality of fingers 130 is received within a respective one of the staple pockets 126 of the staple cartridge 122 and is movable through the respective staple pocket 126 to eject the staples 124 from the staple pockets 126 when the staple pushing member 116 is moved from its retracted position to its advanced position within the shell housing 110.

The shell housing 110 includes a proximal portion 136 (FIG. 2) that supports a coupling mechanism 140 that is operable to releasably couple the reload assembly 100 to the adapter assembly 14 of the stapling device 10 (FIG. 1) to facilitate replacement of the reload assembly 100 and reuse of the stapling device 10. The coupling mechanism 140 includes a retaining member 142 and a coupling member 144. The coupling member 144 is received about the proximal portion 136 (FIG. 2) of the shell housing 110 and engages the distal portion 14a (FIG. 3) of the adapter assembly 14 to couple the reload assembly 100 to the adapter assembly 14. It is envisioned that other coupling mechanisms can be used to secure the reload assembly 100 to the adapter assembly 14.

The shell housing 110 includes an outer annular body portion 150 and an inner annular body portion 152 that are coupled to each other and define an annular cavity 154 within the shell housing 110. The inner annular body portion 152 defines a through bore 158 that receives the anvil retainer 24 of the adapter assembly 14 and facilitates movement of the anvil retainer 24 from an advanced position to a retracted position. The anvil retainer 24 is releasably coupled to the anvil assembly 18 and movable between its advanced and retracted positions to move the anvil assembly 18 in relation to the staple cartridge 122 between the open and clamped positions. The annular pusher 114, staple pushing member 116, knife carrier 118, and annular knife 120 are supported within the annular cavity 154 of the shell housing 110 and are movable between their retracted and advanced positions to eject the staples 124 from the reload assembly 100 and cut tissue clamped between the anvil assembly 18 and the staple cartridge 122. The '495 Publication discloses operation of an exemplary reload assembly including an annular pusher, a staple pushing member, a knife carrier, and an annular knife.

The reload assembly 100 includes a bushing 160 (FIG. 2) that is supported on the inner annular body portion 152 of the shell housing 110. In aspects of the disclosure, the bushing 160 includes a substantially cylindrical body that defines a through bore 162 and includes a distal portion 164, a proximal portion 166, and a flange 168 positioned between the distal body portion 164 and the proximal body portion 168. The through bore 162 is axially aligned with the through bore 158 of the inner annular body portion 152 of the shell housing 110. The distal body portion 164 includes a plurality of raised retaining rings 170 that extend about an outer surface of the bushing 160. The distal portion 164 of the bushing 160 is received within the through bore 158 in a proximal end of the inner annular body portion 152 of the shell housing 110. The retaining rings 170 engage an inner surface of the inner annular body portion 152 (FIG. 4) to secure the bushing 160 to the shell housing 110.

Figure 3:
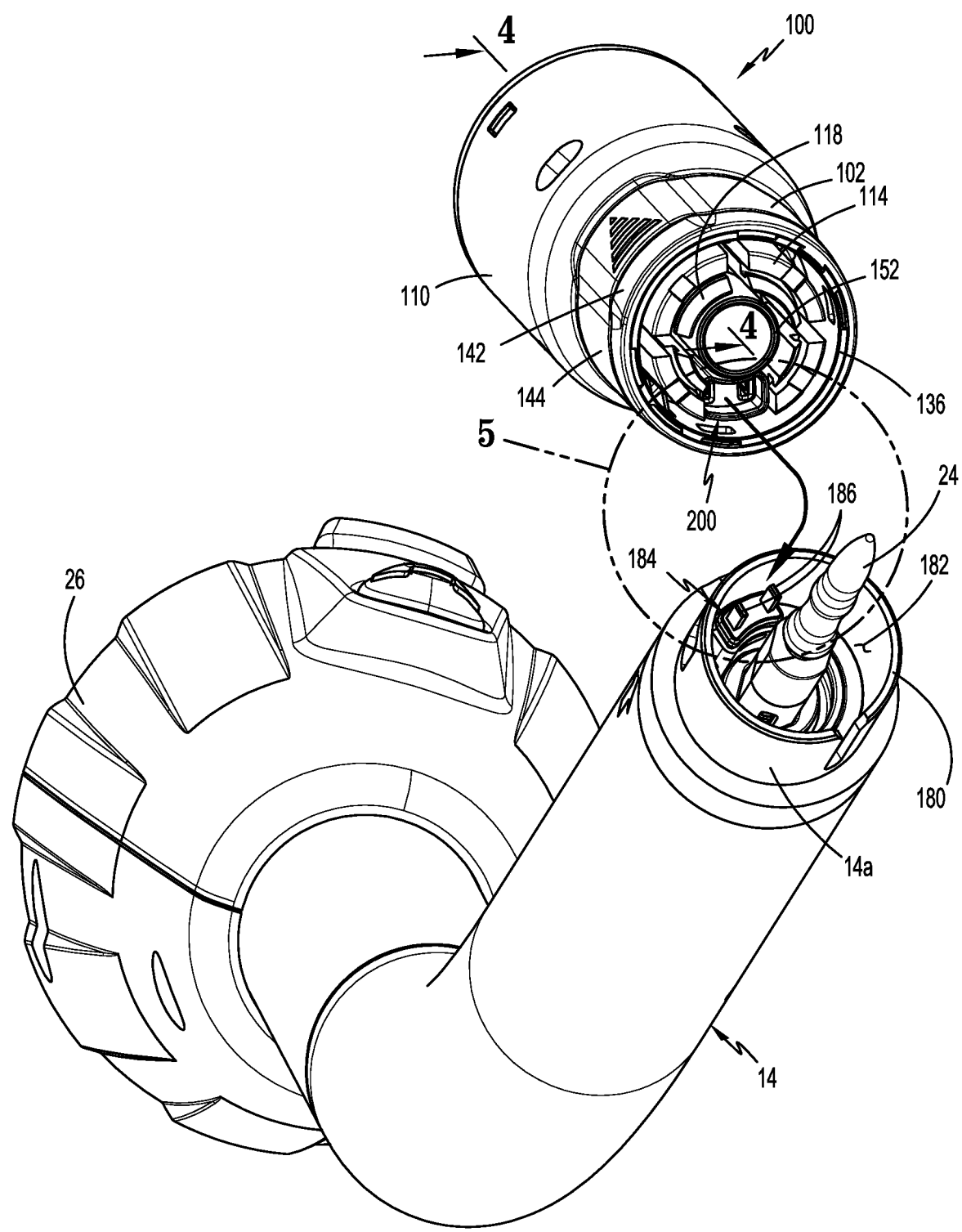
FIG. 3 is a perspective view of an adapter assembly and reload assembly of the surgical stapling device shown in FIG. 1 with the reload assembly separated from the adapter assembly.
Figure 4:
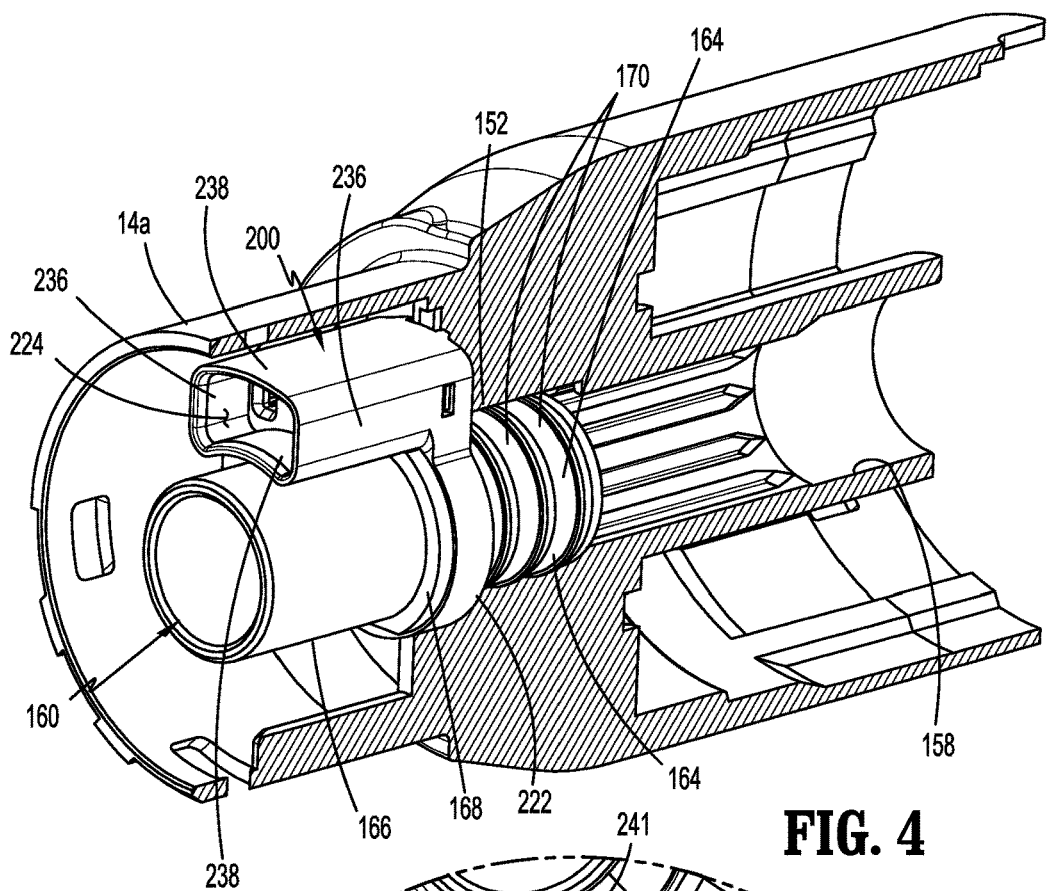
FIG. 4 is a cross sectional view taken along section line 4-4 of FIG. 3.
Figure 5:
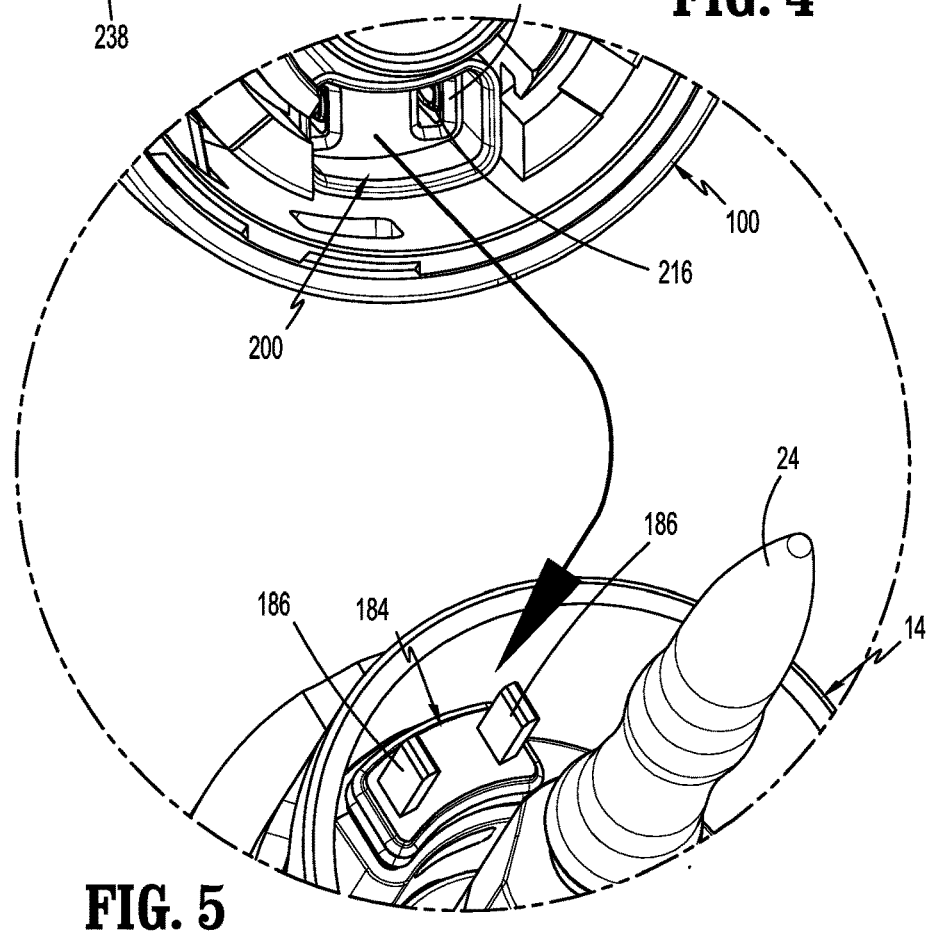
FIG. 5 is an enlarged view of the indicated area of detail shown in FIG. 3.
Figure 6:
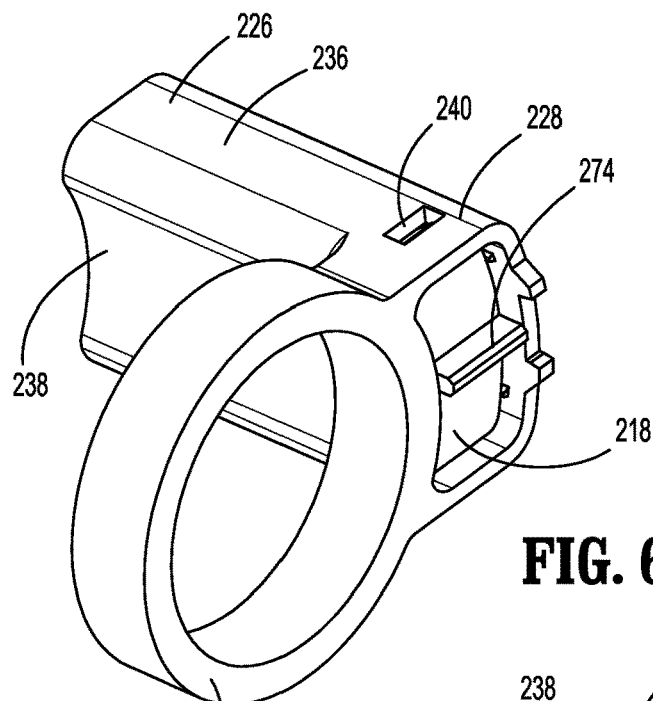
FIG. 6 is an enlarged view of the indicated area of detail shown in FIG. 2.
Figure 7:
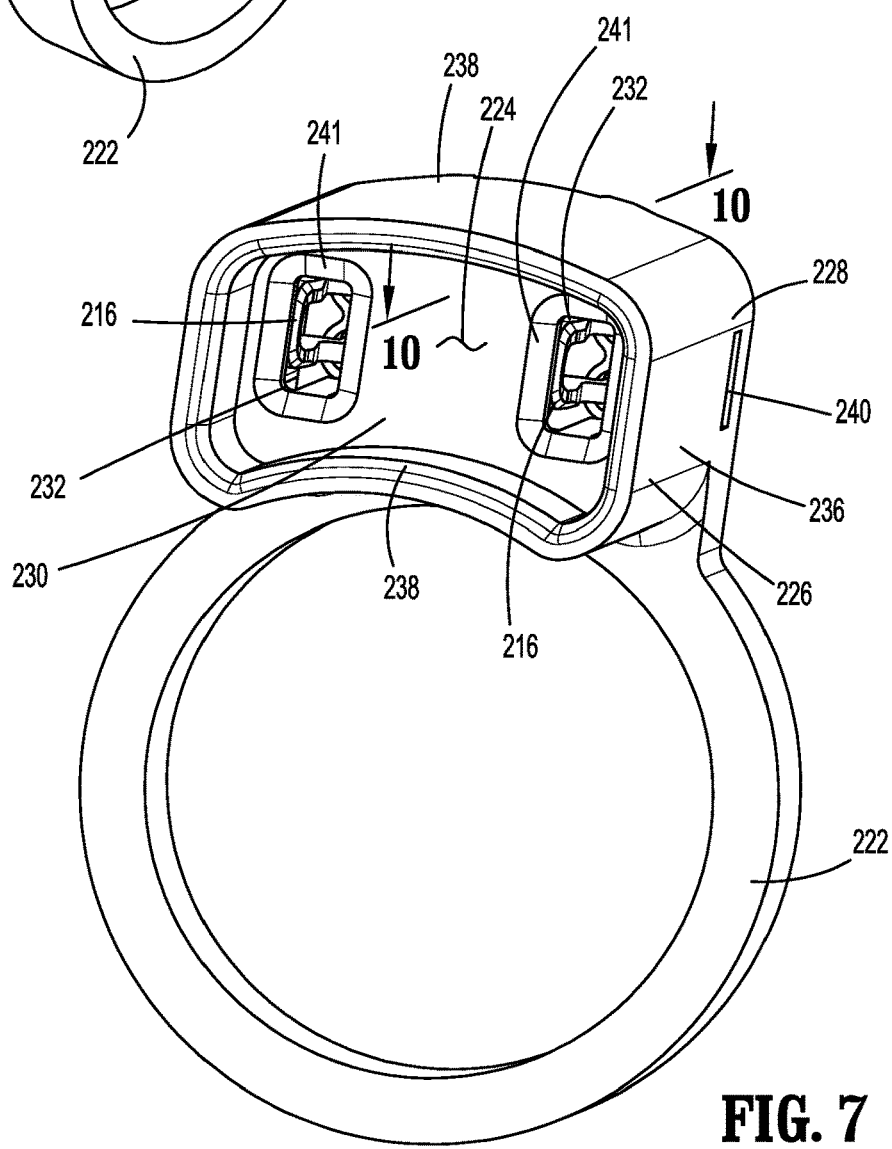
FIG. 7 is a side perspective view of an authentication chip and printed circuit board ("PCB") assembly of the reload assembly shown in FIG. 3.
Figure 8:
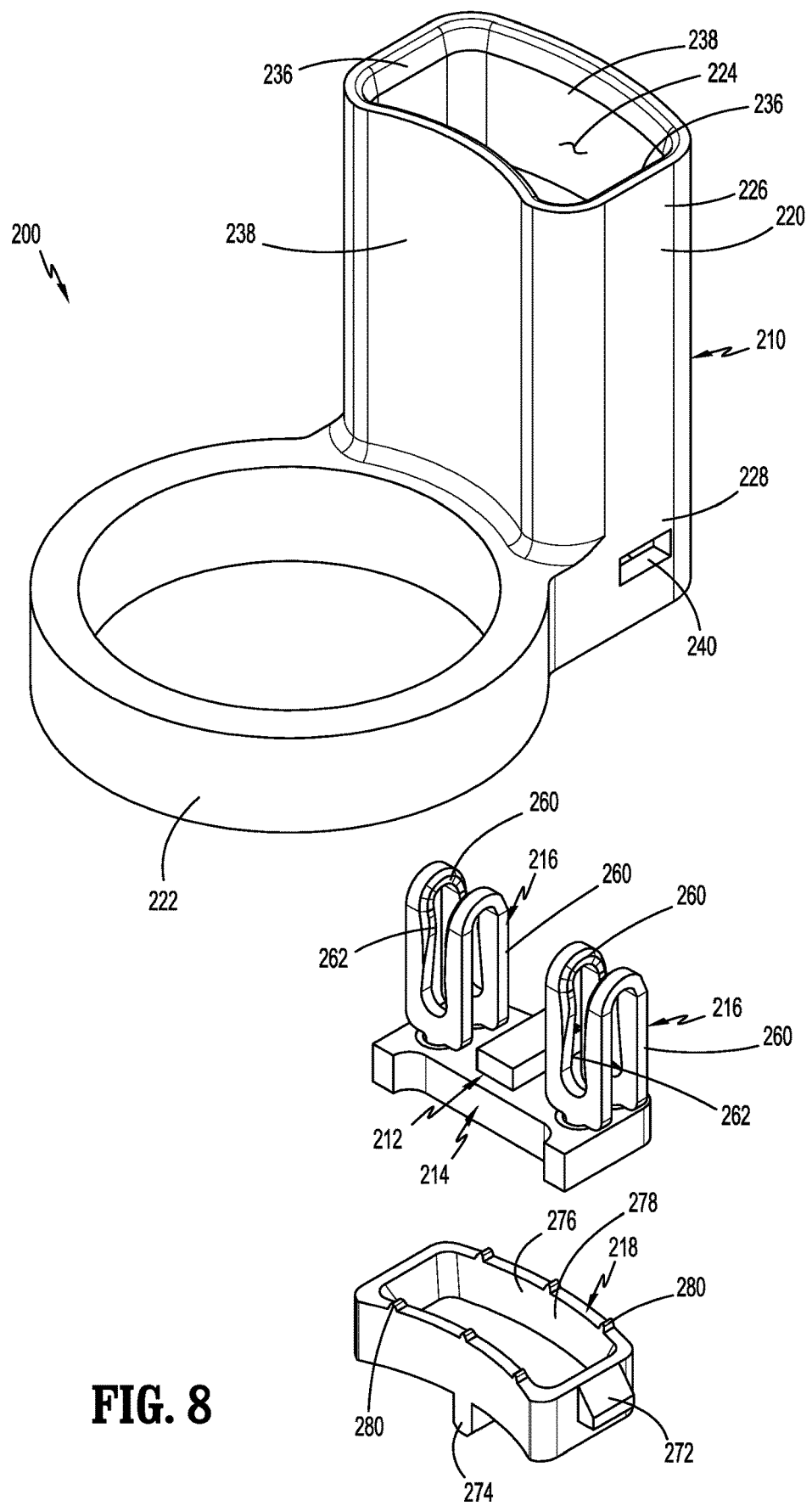
FIG. 8 is a side perspective exploded view of the authentication chip and PCB assembly shown in FIG. 7.
Figure 9:
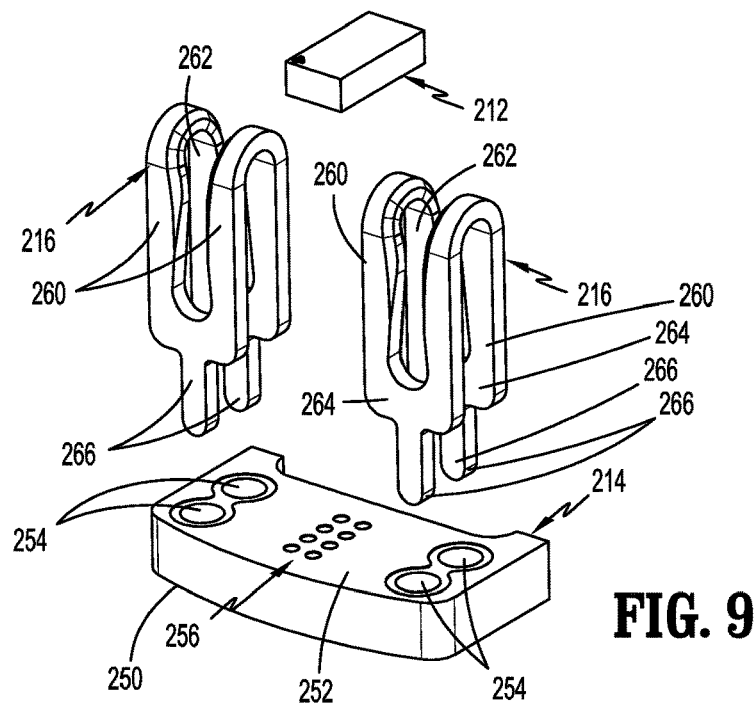
FIG. 9 is a side perspective view of the authentication chip, PCB, and electrical contacts of the authentication chip and PCB assembly shown in FIG. 8 with parts separated.

FIGS. 3-5 illustrate a proximal portion of the reload assembly 100 which includes an authentication chip and printed circuit board (PCB) assembly shown generally as chip and PCB assembly 200. In aspects of the disclosure, the chip and PCB assembly 200 is secured to the inner annular body portion 152 of the shell housing 110 by the bushing 160 as described below.

FIGS. 3 and 5 illustrate a distal portion 14a of the adapter assembly 14 which includes a tubular body 180 that defines a channel 182. The anvil retainer 24 extends from the distal end of the tubular body 180 along a central longitudinal axis of the tubular body 180. The adapter assembly 14 includes a plug 184 that includes spaced conductive prongs 186 that are positioned within the tubular body 180 and extend in a distal direction within the channel 182 of the tubular body 180. The plug 186 is connected by a conductor, e.g., wires or an electrical ribbon, to a controller supported within the handle assembly 12. The conductor (not shown) extends from the plug 184 within the elongate body 14 towards the handle assembly 12 to allow the reload assembly to communicate with the controller positioned within the handle assembly 12. As used herein, the term "controller" includes a processor, a digital processing device and like terms used to indicate a microprocessor or central processing unit (CPU). A CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed stapling device 10 and provides services for execution of applications for use with the disclosed stapling device 10. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects of the disclosure, the operating system is provided by cloud computing.

FIGS. 6-12 illustrate the chip and PCB assembly 200 which includes a housing 210, an authentication chip 212, a PCB 214 having electrical contacts 216, and a closure member or cap 218. The housing 210 includes a body 220 and a securement ring 222 secured to one end of the body 220. The body 220 defines a cavity 224 and has open proximal and distal portions 226 and 228, respectively, that communicate with the cavity 224. The body 220 of the housing 210 includes a transverse wall 230 (FIG. 10) that extends across the cavity 224 and includes two spaced openings or ports 232. The transverse wall 230 is positioned in a proximal portion of the cavity 224 of the housing 210. The openings 232 are defined in part by tapered walls 241 (FIG. 10) that are angled in the distal direction into the openings 232. The openings 232 receive the conductive prongs 186 of the plug 184 of the adapter assembly 14 when the reload assembly 100 is coupled to the adapter assembly 14 as described below.

The body 220 of the housing 210 of the chip and PCB assembly 200 includes side walls 236 and upper and lower walls 238 (as viewed in FIG. 4) that connect the side walls 236 to each other to define the cavity 224 of the housing 210. Each of the side walls 236 defines an opening 240 (FIG. 8) in the distal portion of the body 220 of the housing 210. An inner surface of the walls 236 and 238 include alignment ribs 241 (FIG. 11) that center the PCB 214 within the housing 210 as described below. In aspects of the disclosure, the housing 210 can be formed from a medical grade plastic material.

The securement ring 222 of the housing 210 is received about the distal portion 164 (FIG. 4) of the bushing 160 of the reload assembly 100 during assembly of the reload assembly 100 before the bushing 160 is inserted into a proximal end of the through bore 158 of the inner annular body portion 152 of the shell housing 110 (FIG. 4). When the bushing 160 is inserted into the through bore 158, the securement ring 222 is compressed between the flange 168 of the bushing 160 and the inner annular body portion 152 of the shell housing 110 to secure the chip and PCB assembly 200 to the shell housing 210. Alternately, it is envisioned that the chip and PCB assembly 200 can be secured within the shell housing 110 using a variety of different securement techniques.

The PCB 214 includes a body 250 that has a proximal surface 252 that defines two bores 254 on each end of the body 250. The body 250 includes a central portion that supports pads 256 for the authentication chip 212 and a distal surface 258 opposite to the proximal surface. In aspects of the disclosure, the body 250 of the PCB 214 is a laminate formed of one or more layers of non-conductive materials and chemically etched copper which produces conductive pathways and the pads 256. In some aspects of the disclosure, the body 250 of the PCB 214 has a top layer of solder mask (e.g., about 0.005 inches), a conductive copper layer (e.g., about 0.007 inches thick), a dielectric layer (e.g., about 0.0315 inches thick), a bottom copper conductive layer (e.g., about 0.007 inches thick), and a bottom layer of solder mask (e.g., about 0.005 inches thick). In certain aspects of the disclosure, the dielectric layer is formed from fiberglass, e.g., FR-4 fiberglass, although other dielectric materials are envisioned.

Figure 10:
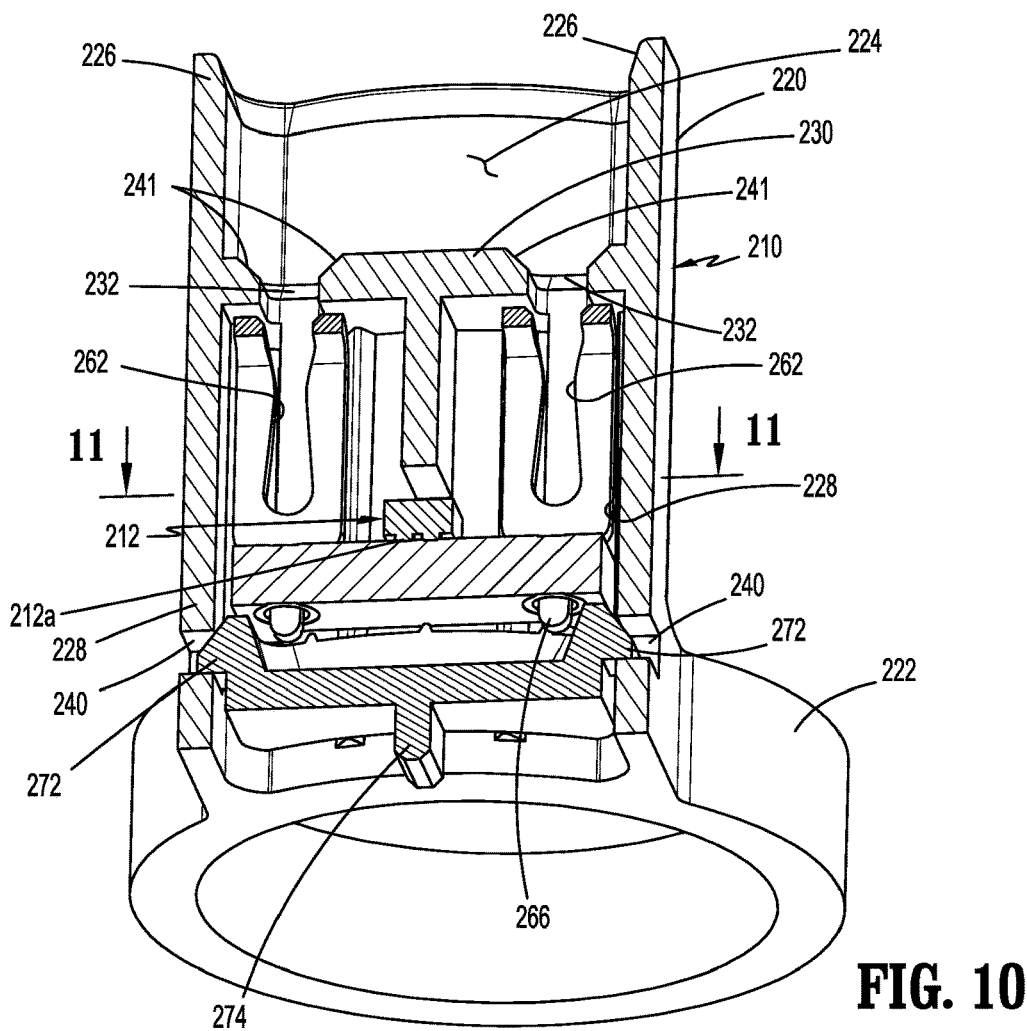
FIG. 10 is a cross-sectional view taken along section line 10-10 of FIG. 7.
Figure 11:
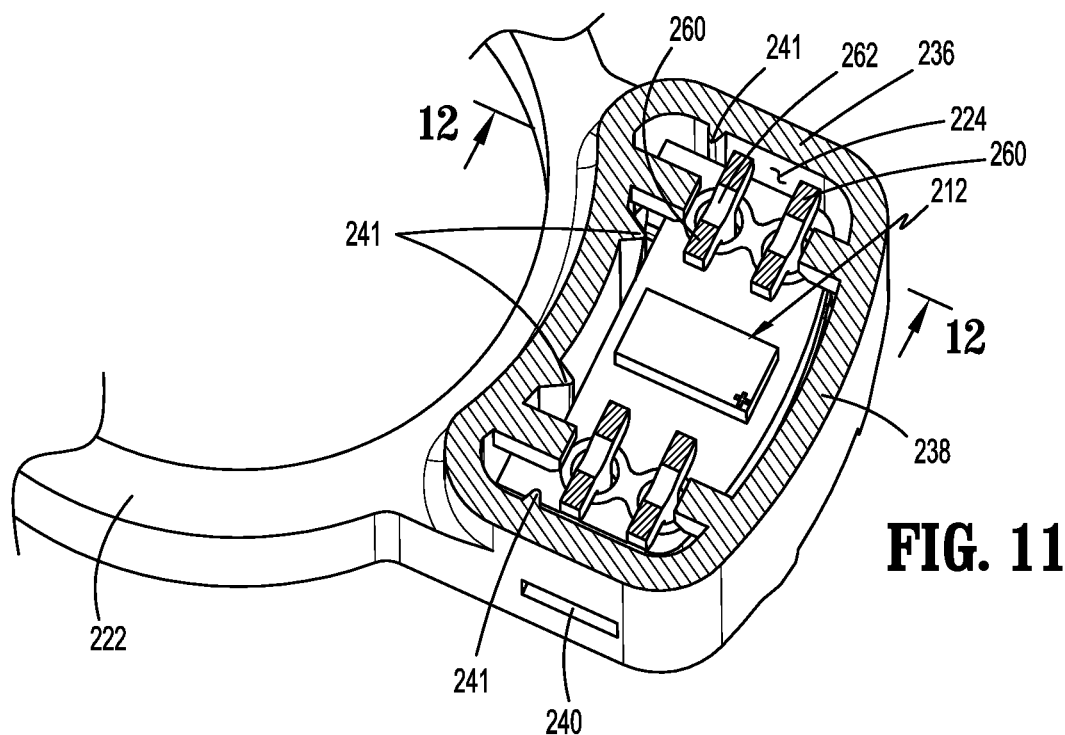
FIG. 11 is a cross-sectional view taken along section line 11-11 of FIG. 10.
Figure 12:
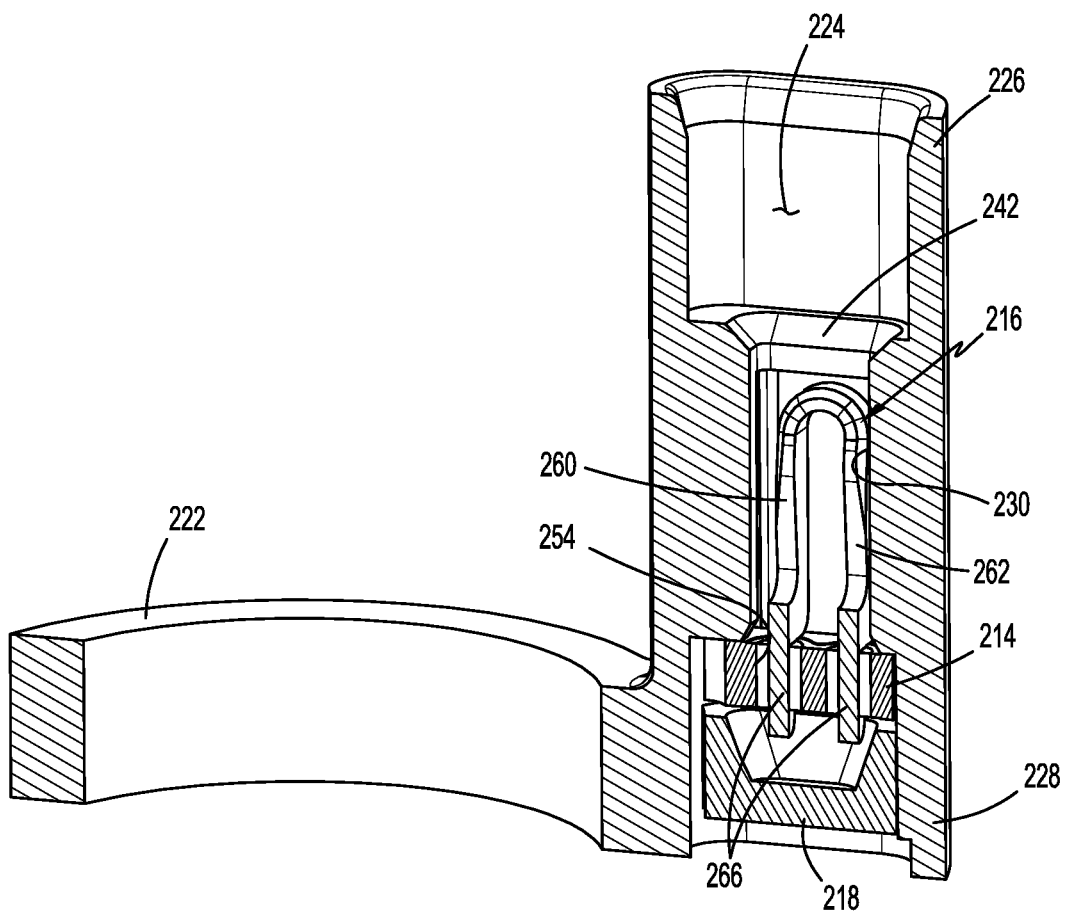
FIG. 12 is a cross-sectional view taken along section line 12-12 of FIG. 11.

The electrical contacts 216 have a folded tuning fork shape. More particularly, each of the electrical contacts 216 includes two elongate contact portions 260 that are spaced to define a slot 262. In aspects of the disclosure, each of the elongate contact portions 260 is substantially U-shaped and includes ends that are coupled together by a base portion 264. Each of the base portions 264 of each of the contact portions 260 includes a prong 266 that is received within one of the bores 254 in the proximal surface 252 of the body 250 of the PCB 214. In aspects of the disclosure, the prongs 266 are soldered to the body 250 of the PCB 214 using known processes. In certain aspects of the disclosure, the elongate contact portions 260 are configured such that a width of the slots 262 initially converges and then subsequently diverges (FIG. 10). This configuration creates a wiping action when the conductive prongs 186 of the plug 184 of the adapter assembly 14 (FIG. 5) are inserted into the slots 262 as described in further detail below.

The chip 212 is positioned on the pads 256 of the body 250 of the PCB 214. In aspects of the disclosure, the bottom of the chip 212 includes solder balls 212a that are placed on the pads 256 and soldered to the pads 256 to secure the chip 212 to the PCB 214. In some aspects of the disclosure, the assembly of the PCB 214 and chip 212 is placed into a solder reflow oven to melt the solder and fuse the solder balls 212a on the bottom of the chip 212 onto the pads 256 of the PCB 214. After the reflow oven, the prongs 266 of the electrical contacts 216 are placed into the bores 254 in the body 250 of the PCB 214 and the assembly is placed within a wave solder machine to bottom solder the prongs 266 of the electrical contacts 216 to the PCB 214. The copper pathways within the PCB 214 electrically couple the electrical contacts 216 to the chip 212. Alternately, it is envisioned that the components of the chip and PCB assembly 200 could be hand soldered.

The cap 218 includes a body 270 that includes tabs 272 (FIG. 8) that extend radially outwardly from each end of the body 270. The body 270 also includes a grip 274 that extends axially from a distal end of the cap 218 to allow the cap 218 to be gripped and assembled to the housing 210 of the chip and PCB assembly 200 as described in further detail below. The tabs 272 are received within the openings 240 in the housing 210 in a snap-fit manner to secure the cap 218 to the housing 210. In aspects of the disclosure, the cap 218 has an open end 276 (FIG. 8) that is defined by a side wall 278 that has a proximal surface that supports a series of spacers 280. The spacers 280 engage the body 250 of the PCB 214 to secure the PCB 214 within the housing 210 of the chip and PCB assembly 200. The alignment ribs 241 (FIG. 11) on the inner surface of the walls 236 and 238 of the housing 210 engage and center or properly position the PCB 214 within the housing 210.

In order to assemble the chip and PCB assembly 200, the PCB 214 with the electrical contacts 216 and the authentication chip 212 mounted thereto is inserted into the open distal portion 228 of the housing 210 of the chip and PCB assembly 200 with the slots 262 of the electrical contacts 216 aligned with the openings 232 in the transverse wall 230 of the housing 210. After the PCB 214 is inserted into the housing 210, the cap 218 is inserted into the open distal portion 228 of the housing 210 and into engagement with the PCB 214 to press the electrical prongs 216 into engagement with the transverse wall 230 of the housing 210. When the tabs 272 are aligned with the openings 240 in the housing 210, the tabs 272, which are deformed inwardly as the cap 218 is inserted into the housing 210, snap outwardly into the openings 240 of the housing 210 to secure the cap 218 and the PCB 214 within the housing 210 of the chip and PCB assembly 200.

It is envisioned that structure other than the cap 218 can be used to secure the components of the PCB assembly 200 within the housing 210. For example, the distal end of the housing 210 can be back-filled with an epoxy to secure the components of the PCB assembly 2200 in place within the housing 210.

Figures 13, 14:
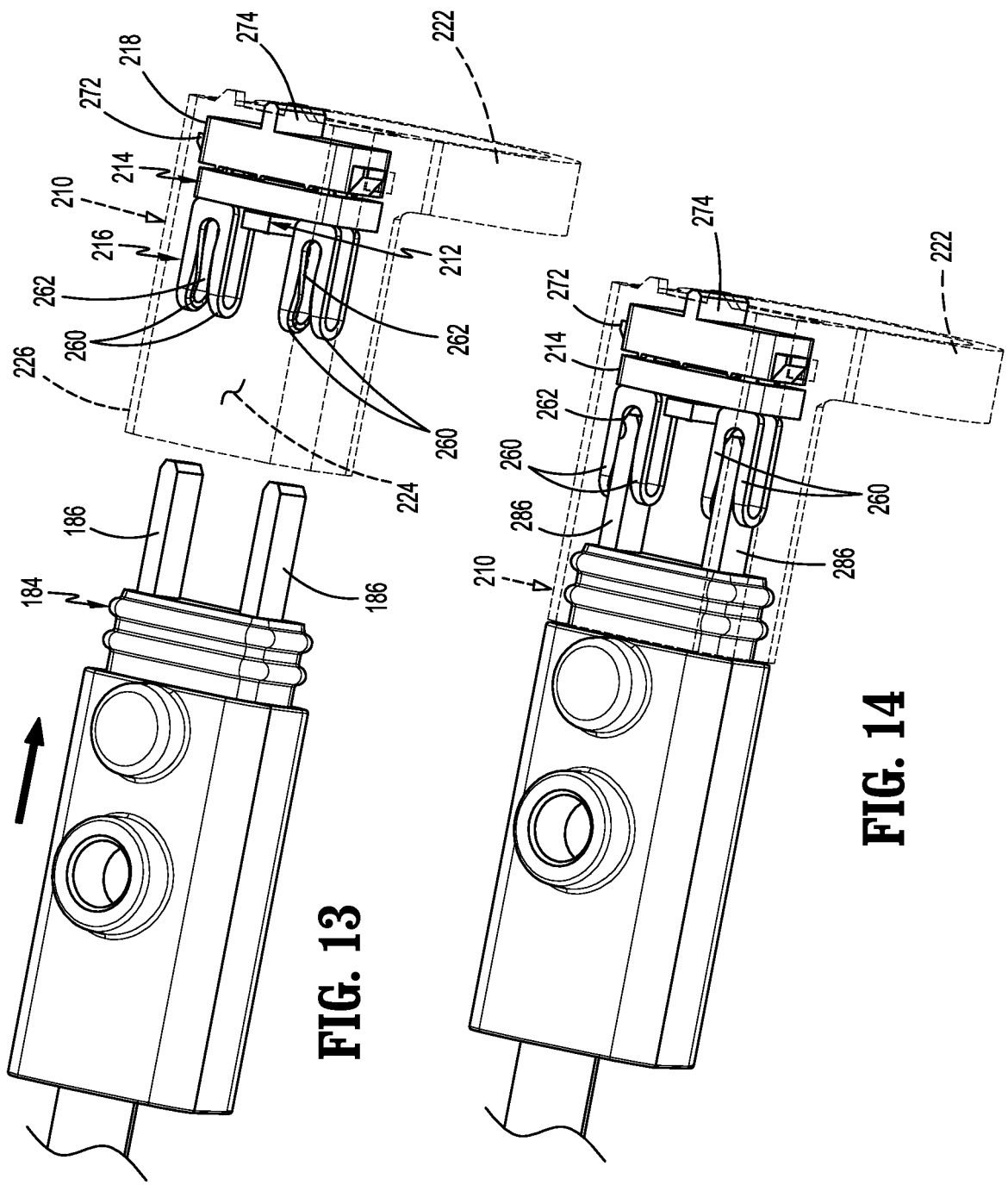
FIG. 13 is a side perspective view of mating plug prongs of the adapter assembly shown in FIG. 2 positioned adjacent the authentication chip and PCB assembly shown in FIG. 7 with the part separated and a housing of the authentication chip and PCB assembly shown in phantom.
FIG. 14 is a side perspective view of the mating plug prongs of the adapter assembly shown in FIG. 2 coupled to the authentication chip and PCB assembly shown in FIG. 7 with the housing of the authentication chip and PCB assembly shown in phantom.

FIGS. 5, 13, and 14 illustrate the plug 184 of the adapter assembly 14 (FIG. 5) as the plug 184 is coupled to the chip and PCB assembly 200 which occurs when the reload assembly 100 is coupled to the adapter assembly 14 (FIG. 5). When the reload assembly 14 is coupled to the adapter assembly 14 (FIG. 5), the conductive prongs 186 extend through the openings 232 (FIG. 10) in the transverse wall 230 of the housing 210 and move into the slots 262 of the elongate contact portions 260 of the electrical contacts 216. The tapered walls 241 defining the openings 232 in the housing 210 of the chip and PCB assembly 200 direct the conductive prongs 186 into the slots 262. As described above, the converging-diverging configuration of the slots 262 defined by the elongate contact portions 260 of each of the electrical contacts 216 creates a wiping action between the conductive prongs 186 and the electrical contacts 216 to remove any contaminants from the components.

In known devices, the electrical contacts of the authentication and printed circuit board assembly are mounted to the housing of the assembly and an authentication chip is soldered directly to the electrical contacts with a solder paste. Subsequently, the assembly is passed through a solder reflow oven and the chip is encapsulated in epoxy within the housing. Due to the large thermal mass of the contacts, flowing of solder between the chip and the contacts is inconsistent and difficult to detect. As a result, the manufacturing yields are low, the soldering joints are poor, and the electrical connections between the electrical contacts and the chip are intermittent. The construction of the chip and PCB assembly 200 described above provides electrical contacts that are self-supporting to allow for automated assembly of the electrical contacts. This construction also provides a more reliable robust electrical connection between the electrical contacts 216 and the chip 212.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A chip and printed circuit board assembly comprising:
a housing including a body defining a cavity and having open proximal and distal ends communicating with the cavity, the body including a transverse wall, the transverse wall extending across the cavity and having a proximal side and a distal side, the transverse wall defining spaced openings that extend through the transverse wall and are configured to receive conductive prongs of a plug;
a printed circuit board supported within the cavity of the housing on the distal side of the transverse wall;
an authentication chip supported on and electrically coupled to the printed circuit board;
electrical contacts supported on and electrically coupled to the printed circuit board, each of the electrical contacts defining a slot, the slots being aligned with the openings in the transverse wall and dimensioned to receive the conductive prongs of the plug; and
a closure member received within the distal end of the body, the closure member engaging the printed circuit board to retain the printed circuit board, the authentication chip, and the electrical contacts within the cavity.

2. The chip and printed circuit board assembly of claim 1, wherein the body is defined by walls, the walls having inner surfaces that include alignment ribs that engage and properly position the printed circuit board within the housing.

3. The chip and printed circuit board assembly of claim 1, wherein the body includes walls defining wall openings and the closure member includes a cap having tabs, the tabs received within the wall openings in a snap-fit manner to secure the cap to the housing.

4. The chip and printed circuit board assembly of claim 1, wherein each of the electrical contacts has a tuning fork shape and includes first and second elongate contact portions that are spaced from each other to define the slot of the respective electrical contact.

5. The chip and printed circuit board assembly of claim 4, wherein the first and second elongate contact portions of each of the electrical contacts are configured to define the slot to have a converging-diverging configuration.

6. The chip and printed circuit board assembly of claim 5, wherein the first and second elongate contact portions of each of the electrical contacts are connected by a base, the base of each of the electrical contacts having a prong.

7. The chip and printed circuit board assembly of claim 6, wherein the printed circuit board defines bores, each of the bores receiving one of the prongs of the electrical contacts.

8. The chip and printed circuit board assembly of claim 1, wherein the printed circuit includes a surface having support pads, the authentication chip being soldered to the support pads.

9. The chip and printed circuit board assembly of claim 1, wherein the transverse wall includes tapered walls that define the openings in the transverse wall, the tapered walls tapering inwardly towards the openings in the transverse wall in a distal direction.

10. The chip and printed circuit board assembly of claim 1, wherein the housing includes a securement ring configured to secure the chip and printed circuit board assembly to a surgical device.

11. A reload assembly comprising:
a shell housing including an outer annular body portion and an inner annular body portion that define an annular cavity;
a staple cartridge supported on the shell housing, the staple cartridge supporting a plurality of staples;
a pusher assembly supported within the annular cavity, the pusher being movable from a retracted position to an advanced position to eject staples from the staple cartridge; and
a chip and printed circuit board assembly supported on the shell housing, the chip and circuit board assembly including:
a housing including a body defining a cavity and having open proximal and distal ends communicating with the cavity, the body including a transverse wall, the transverse wall extending across the cavity and having a proximal side and a distal side, the transverse wall defining spaced openings that extend through the transverse wall and are configured to receive conductive prongs of a plug of surgical device;
a printed circuit board supported within the cavity of the housing on the distal side of the transverse wall;
an authentication chip supported on and electrically coupled to the printed circuit board;
electrical contacts supported on and electrically coupled to the printed circuit board, each of the electrical contacts defining a slot, the slots being aligned with the openings in the transverse wall and dimensioned to receive the conductive prongs of the plug; and
a closure member received within the distal end of the body, the closure member engaging the printed circuit border to retain the printed circuit board, the authentication chip, and the electrical contacts within the cavity.

12. The reload assembly of claim 11, wherein the housing of the chip and printed circuit board assembly includes a securement ring, the securement ring configured to secure the housing of the chip and printed circuit board assembly to the inner annular body portion of the shell housing.

13. The reload assembly of claim 11, wherein the body is defined by wall, the walls having inner surfaces that include alignment ribs that engage and properly position the printed circuit board within the housing.

14. The reload assembly of claim 11, wherein the body includes walls defining wall openings and the closure member includes a cap having tabs, the tabs received within the wall openings in a snap-fit manner to secure the cap to the housing.

15. The reload assembly of claim 11, wherein each of the electrical contacts has a tuning fork shape and includes first and second elongate contact portions that are spaced from each other to define the slot.

16. The reload assembly of claim 15, wherein the first and second elongate contact portions of each of the electrical contacts are configured to define the slot to have a converging-diverging configuration.

17. The reload assembly of claim 16, wherein the first and second elongate contact portions of each of the electrical contacts are connected by a base, the base of each of the electrical contacts having a prong.

18. The reload assembly of claim 17, wherein the printed circuit board defines bores, each of the bores receiving one of the prongs of the electrical contacts.

19. The reload assembly of claim 11, wherein the printed circuit includes a surface having support pads, the authentication chip being soldered to the support pads.

20. The reload assembly of claim 11, wherein the transverse wall includes tapered walls that define the openings in the transverse wall, the tapered walls tapering inwardly towards the openings in the transverse wall in a distal direction.

\* \* \* \* \*